(12) United States Patent
Bharat et al.

(10) Patent No.: US 10,953,242 B2
(45) Date of Patent: Mar. 23, 2021

(54) GUIDING TRACKED SHAPE RECONSTRUCTION FOR INTERVENTIONAL PROCEDURES

(71) Applicant: KONINKLIJKE PHILIPS N.V., Eindhoven (NL)

(72) Inventors: Shyam Bharat, Arlington, MA (US); Ehsan Dehghan Marvast, New York, NY (US); Cynthia Ming-Fu Kung, New York, NY (US); Jochen Kruecker, Washington, DC (US); Ananth Ravi, Toronto (CA); Niranjan Venugopal, Toronto (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 401 days.

(21) Appl. No.: 15/533,462

(22) PCT Filed: Nov. 17, 2015

(86) PCT No.: PCT/IB2015/058861
§ 371 (c)(1),
(2) Date: Jun. 6, 2017

(87) PCT Pub. No.: WO2016/092388
PCT Pub. Date: Jun. 16, 2016

(65) Prior Publication Data
US 2017/0368368 A1  Dec. 28, 2017

Related U.S. Application Data

(60) Provisional application No. 62/090,019, filed on Dec. 10, 2014.

(51) Int. Cl.
*A61B 17/00* (2006.01)
*A61B 34/20* (2016.01)
(Continued)

(52) U.S. Cl.
CPC ......... *A61N 5/1048* (2013.01); *A61N 5/1007* (2013.01); *A61B 34/10* (2016.02);
(Continued)

(58) Field of Classification Search
CPC .......... A61B 34/10; A61B 2017/00115; A61B 2017/00292; A61B 2034/2051;
(Continued)

(56) References Cited

U.S. PATENT DOCUMENTS 5,592,939 A   1/1997  Martinelli
6,626,832 B1* 9/2003  Paltieli ................ A61B 8/0833
                                                   128/897
(Continued)

FOREIGN PATENT DOCUMENTS

WO     2014013418 A2    1/2014

OTHER PUBLICATIONS

Elgort et al. (2003). Real-Time Catheter Tracking and Adaptive Imaging. J. Magn. Reson. Imaging, 18: 621-626. (Year: 2003).*
(Continued)

*Primary Examiner* — Bill Thomson
*Assistant Examiner* — Younhee Choi
(74) *Attorney, Agent, or Firm* — Sherry Austin

(57) ABSTRACT

An intervention system employs an interventional device (10), and a sensor wire (20) manually translatable within a lumen (11). The intervention system further employs a reconstruction controller (44) for reconstructing a shape of the interventional tool (10) responsive to a sensing of a manual translation of the sensor wire (20) within the lumen (11) (e.g., a EM sensor being attached to/embedded within a guide wire), and for determining a reconstruction accuracy of a translation velocity of the sensor wire (20) within the lumen (11) to thereby facilitate an accurate reconstruction of the shape of the interventional tool (10). The reconstruction
(Continued)

accuracy may be determined by the reconstruction controller (44) as an acceptable translation velocity being less than an acceptable threshold, an unacceptable translation velocity being greater than an unacceptable threshold, and/or a borderline translation velocity being greater than the acceptable threshold and less than the unacceptable threshold. The reconstruction controller (44) generates an acceptability indicator that may be visualizing or audibly communicated via a user interface (48).

14 Claims, 2 Drawing Sheets

(51) Int. Cl.
*A61N 5/10* (2006.01)
*A61B 34/10* (2016.01)

(52) U.S. Cl.
CPC ............... *A61B 2017/00115* (2013.01); *A61B 2017/00292* (2013.01); *A61B 2034/2051* (2016.02); *A61N 2005/1008* (2013.01); *A61N 2005/1051* (2013.01); *A61N 2005/1062* (2013.01); *A61N 2005/1074* (2013.01)

(58) Field of Classification Search
CPC ............... A61N 5/1007; A61N 5/1048; A61N 2005/1008; A61N 2005/1051; A61N 2005/1062; A61N 2005/1074
See application file for complete search history.

(56) References Cited

U.S. PATENT DOCUMENTS

| | | | | |
|---|---|---|---|---|
| 7,020,512 | B2* | 3/2006 | Ritter | A61B 5/06 600/407 |
| 7,811,294 | B2* | 10/2010 | Strommer | A61B 1/00147 606/108 |
| 8,167,805 | B2* | 5/2012 | Emery | A61B 50/13 600/437 |
| 8,512,256 | B2 | 8/2013 | Rothenberg | |
| 8,543,189 | B2 | 9/2013 | Paitel et al. | |
| 8,900,225 | B2* | 12/2014 | Bar-Tal | A61N 1/06 606/34 |
| 2002/0115931 | A1* | 8/2002 | Strauss | A61B 6/12 600/420 |
| 2005/0119646 | A1* | 6/2005 | Scholl | A61B 18/1492 606/32 |
| 2007/0197905 | A1 | 8/2007 | Timinger et al. | |
| 2008/0255475 | A1* | 10/2008 | Kondrosky | A61M 25/09 600/585 |
| 2011/0160571 | A1* | 6/2011 | Cohen | A61B 8/0833 600/424 |
| 2013/0072787 | A1* | 3/2013 | Wallace | A61B 6/487 600/424 |
| 2015/0080712 | A1* | 3/2015 | Van Keersop | A61B 34/20 600/424 |

OTHER PUBLICATIONS

Elgort, D.R. et al., "Real-Time Catheter Tracking and Adaptive Imaging", Journal of Magnetic Resonance Imaging 18:621-626 (2003).

Saikus et al "MRI-Guided Vascular Access With an Active Visualization Needle" Journal of Magnetic Resonance Imaging 34 p. 1159-1166 (2011).

* cited by examiner

GUIDING TRACKED SHAPE RECONSTRUCTION FOR INTERVENTIONAL PROCEDURES

CROSS-REFERENCE TO PRIOR APPLICATIONS

This application is the U.S. National Phase application under 35 U.S.C. § 371 of International Application Serial No. PCT/IB2015/058861, filed on Nov. 17, 2015, which claims the benefit of U.S. Application Ser. No. 62/090,019, filed on Dec. 10, 2014. These applications are hereby incorporated by reference herein.

The present invention generally relates to shape reconstruction of an interventional tool (e.g., a catheter) for interventional procedures (e.g., high dose rate brachytherapy). The present invention specifically relates to a user interface providing an acceptability indication of the shape reconstruction of the interventional tool.

High dose rate ("HDR") brachytherapy is a form of cancer therapy that utilizes high doses of ionizing radiation delivered over a short period of time (e.g., on the order of minutes) directly at or near the anatomical target (e.g., prostate) via hollow treatment channels or catheters. As part of the treatment planning process, the catheter positions relative to the anatomical target are identified and a dose optimization algorithm specifies the dwell positions and dwell times for the radioactive source to thereby achieve a conformal three-dimensional ("3D") dose distribution in the target. The dwell positions and dwell times are then transferred to the treatment delivery device (e.g., a HDR afterloader).

In electromagnetically ("EM") tracked HDR brachytherapy, catheter shapes and poses are determined by manually sliding a flexible EM-tracked wire inside the lumen or hollow channel of the catheter. More particularly, EM data is recorded while retracting the wire from the catheter to thereby serve as a basis for catheter shape reconstruction. During the catheter shape reconstruction, if the EM wire is manually retracted too fast by the user, then the reconstructed catheter shape may not be accurate for a couple of reasons. One reason is an EM acquisition frame rate is limited (e.g., 40 Hz), which sets the resolution of the reconstructed catheter shape. A second reason is the treatment delivery system (e.g., a HDR afterloader) specifies dwell positions at dwell increments for the radioactive source (e.g., 2.5 mm increments), which sets the resolution of the treatment delivery systems.

For accurate catheter shape reconstruction, the resolution of the reconstructed catheter shapes must be at least as high as the resolution of the treatment delivery system. Therefore, the EM tracks should ideally contain data at tracking increments less than the dwell increments particularly with a degree of spatial redundancy to ensure accurate catheter shape reconstruction (e.g., tracking increments of 1 mm to dwell increments of 2.5 mm). This can be achieved by slowing down the manual EM wire retraction speed.

To facilitate an operator of a manual retraction kit adhering to an acceptable "speed limit" while manually retracting the EM wire from the catheter lumen, the present invention provides an accuracy determination of a translation velocity of the sensor wire within the lumen to ensure high quality and accuracy of the reconstructed catheter shapes. The accuracy determination may be communicated to the operator via a user interface indicating an acceptable, unacceptable and/or borderline translation velocity.

One form of the present invention is an intervention system employing an interventional tool having a lumen (e.g., catheter), and a sensor wire translatable within the lumen (e.g., an EM based guide wire). The intervention system further employs a reconstruction controller for reconstructing a shape of the interventional tool responsive to a sensing of a manual translation of the sensor wire within the lumen, and for determining a reconstruction accuracy of a translation velocity of the sensor wire within the lumen to thereby facilitate an accurate reconstruction of the shape of the interventional tool.

The reconstruction accuracy may be determined by the reconstruction controller as an acceptable translation velocity being less than an acceptable threshold, an unacceptable translation velocity being greater than an unacceptable threshold, and/or a borderline translation velocity being greater than the acceptable threshold and less than the unacceptable threshold. The reconstruction controller generates an acceptability indicator visualizing or audibly communicated via a user interface.

For purposes of the present invention, the term "interventional tool" broadly encompasses all tools, instruments, etc. known prior to and subsequent to the present invention having a structurally configuration with a lumen (a.k.a., a channel, a passage, etc.) utilized in any interventional procedure for shape reconstruction of the interventional tool. Examples of an interventional tool include, but are not limited to, a catheter (plastic/metal), a hollow needle and cannula.

For purposes of the present invention, the term "sensor wire" broadly encompasses all wires known prior to and subsequent to the present invention having a structurally configuration with a sensor of any type attached thereto/embedded therein for sensing the wire as the wire is utilized for shape reconstruction of an interventional tool. Examples of a sensor wire include, but are not limited to, a medical guide wire having an electro-magnetic sensor attached to/embedded within a distal tip of the medical guide wire.

For purposes of the present invention, the term "reconstruction controller" broadly encompasses all structural configurations of a specific purpose main board or an application specific integrated circuit housed within or linked to a computer for controlling an implementation of various inventive principles of the present invention as subsequently described herein. The structural configuration of the reconstruction controller may include, but is not limited to, processor(s), computer-usable/computer readable storage medium(s), an operating system, application module(s), peripheral device controller(s), slot(s) and port(s). Examples of a computer includes, but is not limited to, a server computer, a client computer, a workstation and a tablet.

For purposes of the present invention, the term "application module" broadly encompasses a structural configuration of electronic circuits/hardware and/or an executable program (e.g., software and/or firmware) of the reconstruction controller for executing a specific application.

A second form of the present invention is the reconstruction controller including a shape reconstruction module for reconstructing a shape of the interventional tool responsive to a sensing of a manual translation of the sensor wire within the lumen, and a reconstruction accuracy module for determining a reconstruction accuracy of a translation velocity of the sensor wire within the lumen to thereby facilitate an accurate reconstruction of the shape of the interventional tool by the shape reconstruction module.

A third form of the present invention is an interventional method involving (1) the sensor wire being manually translated within the lumen of the interventional tool, (2) the reconstruction controller reconstructing the shape of the interventional tool responsive to the sensing of the manual translation of the sensor wire within the lumen, and (3) the reconstruction controller determining a reconstruction accuracy of a translation velocity of the sensor wire within the lumen to thereby facilitate an accurate reconstruction of the shape of the interventional tool.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

To facilitate an understanding of the present invention, exemplary embodiments of the present invention will be provided herein directed to a shape reconstruction of a catheter 10 accomplished by a manual retraction of a guide wire 20 through a lumen 11 of catheter 10 as the manual retraction of the guide wire 20 is sensed via an EM sensor 31 attached to/embedded within a distal tip of guide wire 20. From the description of the exemplary embodiments of the present invention, those having ordinary skill in the art will appreciate how to make and use the present invention for any type of interventional procedure (e.g., a biopsy and a brachytherapy) involving a shape reconstruction of any interventional tool accomplished by a sensing of a translation (i.e., extension or retraction) of a sensor wire through a lumen of the interventional tool.

For purposes of the present invention, the terms of the art including, but not limited to, "shape reconstruction", "electromagnetic field generator", "manual retraction kit", "reconstruction spacing" and "electromagnetic sensing points", are to be interpreted as known in the art of the present invention.

Figure 1:
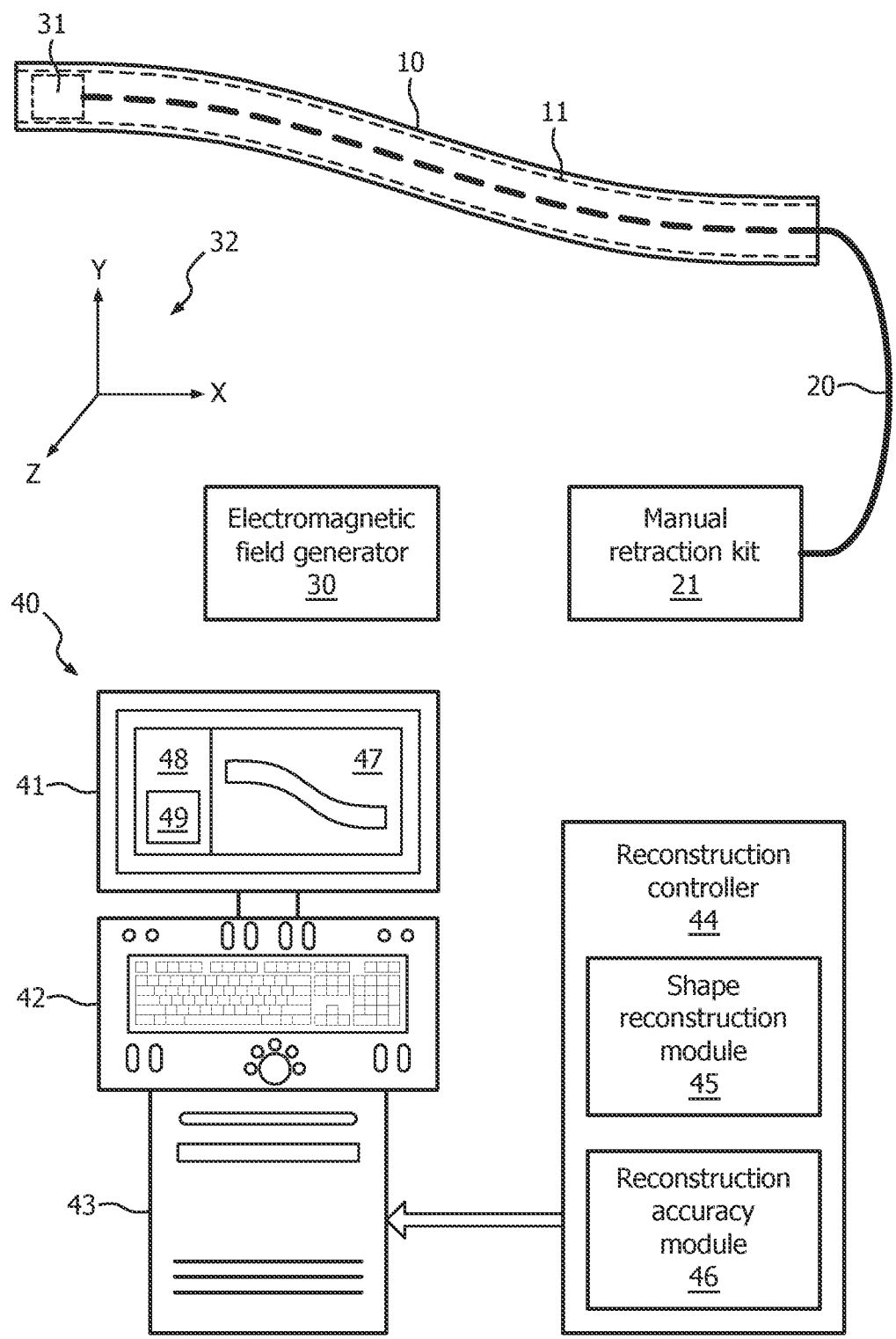
FIG. 1 illustrates an exemplary embodiment of an intervention system in accordance with the present invention.

Referring to FIG. 1, the shape reconstruction of catheter 10 is derived from (1) a utilization of a manual retraction kit 21 having various structural configurations as known in the art for manually retracting guide wire 20 from lumen 11 of catheter 10, and (2) a utilization of an electro-magnetic field generator 30 having various structural configurations as known in the art for generating an electro-magnetic field (not shown) sensed by EM sensor 31 relative to a reference coordinate systems 32.

To this end, an intervention machine 40 for reconstructing the shape of catheter 10 employs a monitor 41, an interface platform 42, a workstation 43 and a reconstruction controller 44 installed within workstation 43.

Reconstruction controller 44 includes and/or is accessible by an operating system (not shown) as known in the art for controlling various graphical user interfaces, data and images on monitor 41 as directed by a workstation operator (e.g., a doctor, technician, etc.) via a keyboard, buttons, dials, joysticks, etc. of interface platform 42, and for storing/reading data as programmed and/or directed by the workstation operator of interface platform 42.

Workstation 43 is connected/coupled to EM sensor 31 as known in the art to receive sensing data to be processed by reconstruction controller 44 for executing an accurate shape reconstruction of catheter 10 in accordance with the present invention. Generally, the sensing data indicates a sensing of a manual retraction of guide wire 20 within lumen 11 via EM sensor 31. In response thereto, reconstruction controller 44 determines a reconstruction accuracy of a translation velocity of guide wire 20 within lumen 11 as the shape of catheter 10 is being reconstructed by reconstruction controller 44.

In one embodiment as shown in FIG. 1, reconstruction controller 44 includes a shape reconstruction module 45 for reconstructing the shape of catheter 10 via the sensing data as known in the art, and a reconstruction accuracy module 46 for determining a reconstruction accuracy of the translation velocity of guide wire 20 within lumen 11 in accordance with a reconstruction accuracy determination method of the present invention. In practice, modules 45 and 46 may be segregated as shown in FIG. 1, or partially integrated for determining a reconstruction accuracy the translation velocity of guide wire 20 within lumen 11.

Generally, the reconstruction accuracy determination method of the present invention is premised on recognizing a shape reconstruction of an interventional tool as known in the art that encompasses a sequential mapping of reconstructed tool segments in accordance with a specific fixed sensing frequency of the sensor wire, and a reasonable translation velocity of the sensor wire within the lumen of the interventional tool must be maintained in order to achieve a desired reconstruction space of each reconstructed tool segment for accurate shape reconstruction.

For example, catheter 10 as a standard HDR catheter may have a length of 24 cm, of which an active length of 15 cm may be inserted within a patient. A shape reconstruction of the active length of catheter 10 as known in the art may encompass a sequential mapping over 3.75 seconds of reconstructed catheter segments in accordance with a specific fixed sensing frequency of 40 Hz. Consequently, an approximate translation velocity of 4 cm/s as guide wire 20 is manually retracted from lumen 11 must be maintained in order to achieve a desired reconstruction spacing of 1 mm for each catheter segment.

Figure 2:
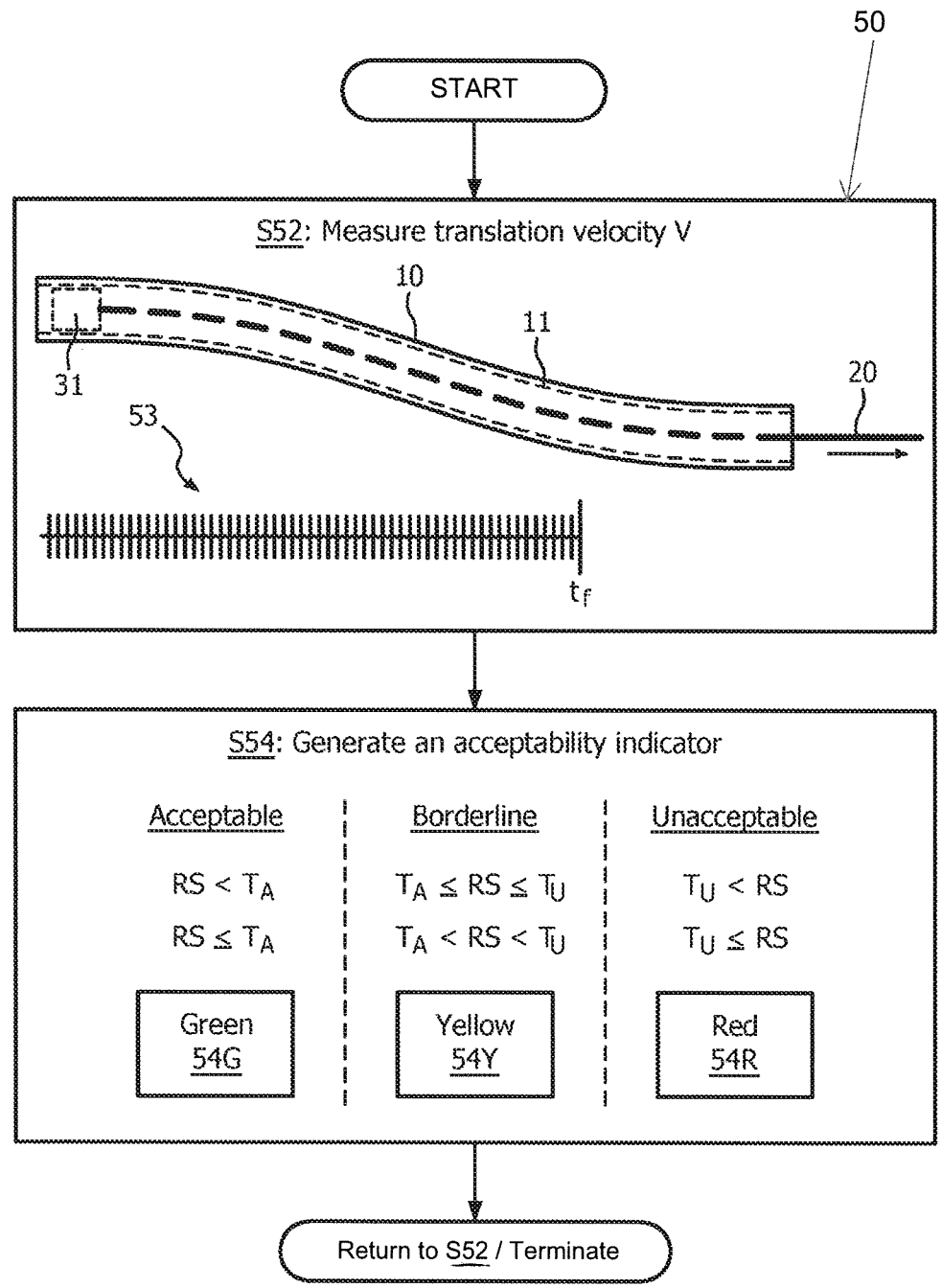
FIG. 2 illustrates a flowchart representative of an exemplary embodiment of a reconstruction accuracy determination method in accordance with the present invention.

In one embodiment of the reconstruction accuracy determination method of the present invention, reconstruction accuracy module 46 executes a flowchart 50 as shown in FIG. 2.

Referring to FIG. 2, a stage S52 of flowchart 50 encompasses reconstruction accuracy module 46 measuring a translation velocity V of a retraction of guide wire 20 from lumen 11 of catheter 10, and a stage S54 of flowchart 50 encompasses reconstruction module 46 generating an acceptability indicator derived from measured translation velocity V relative to accuracy thresholds in the form of an acceptable threshold $T_A$, and an unacceptable threshold $T_U$.

More particularly, the sensing frequency of EM sensor 31 is set. Therefore, a monitoring of reconstruction spacing of between EM sensing points represents a measurement of translation velocity V for each catheter segment. Thus, over a time frame 53 extending from time $t_0$ to time $t_f$, numerous reconstruction spacing of an active length of catheter 10 between EM sensing points symbolized within time frame 53 will be monitored by module 46.

If a monitored reconstruction spacing RS between EM sensing points is less than acceptable threshold $T_A$ (e.g., 1 mm) (or alternatively less than or equal to acceptable threshold $T_A$), then the measured translation velocity V is considered acceptable by module 46 and an acceptable indicator is generated and displayed. In one embodiment, the acceptable indicator may be a green color coded acceptable indicator 54G.

If a monitored reconstruction spacing RS between EM sensing points is equal to or greater than acceptable threshold $T_A$ (e.g., 1 mm) and is less than or equal to unacceptable threshold $T_U$ (e.g., 2 mm) (or alternatively greater than acceptable threshold $T_A$ and/or less than unacceptable threshold $T_U$), then the measured translation velocity V is considered borderline by module 46 and a borderline indicator is generated and displayed. In one embodiment, the borderline indicator may be a yellow color coded acceptable indicator 54Y.

If a monitored reconstruction spacing RS between EM sensing points is greater than greater than unacceptable threshold $T_U$ (e.g., 2 mm) (or alternatively equal to or greater than unacceptable threshold $T_U$), then the measured translation velocity V is considered unacceptable by module 46 and an unacceptable indicator is generated and displayed. In one embodiment, the unacceptable indicator may be a red color coded acceptable indicator 54R.

In practice, the measurement of translation velocity V may be based on each successive EM sampling point. Alternatively, the measurement of translation velocity V may be based on a filtering and smoothing of the raw EM data to avoid "false alarms" introduced by noise in the sensing of EM sensor 31. For example, the measurement of translation velocity V may be based on averaging N samples (e.g. N<=10) in order to provide a more robust estimate of the instantaneous translation velocity V.

Also in practice, reconstruction module 46 may generate an acceptability indicator derived from measured translation velocity V relative to acceptable threshold $T_A$ exclusively or unacceptable threshold $T_U$ exclusively.

Module 46 returns through stage S52 and S54 until a completion of the shape reconstruction of the active length of catheter 10.

Referring back to FIG. 1, reconstruction controller 44 generates and displays a user interface 48 on monitor 44 for visually and/or audibly communicating generated acceptability indicator(s) 49 by module 46 to the workstation operator.

In one embodiment, user interface 48 provides a button to activate/deactivate EM data recording. When activated, a real-time feedback bar 49 becomes active and is instantaneously color coded with the currently generated acceptability indicator by module 46 to communicate the acceptability of the retraction speed of guide wire 20 from lumen 10.

In another embodiment, the user interface 48 alternatively presents a real-time color map of catheter 10 (not shown) that changes color over the map whenever the measured translation velocity V transitions between being acceptable, borderline and/or unacceptable. This will show the workstation operator which part of reconstructed catheter 10 may have lower reconstruction accuracy.

In another embodiment, the display 47 of the reconstructed catheter 10 may be color coded to show which part the reconstructed catheter 10 may have lower reconstruction accuracy.

In practice, to account for variability in different workstation operator, the user interface may be configured to flag a reconstructed catheter 10 even if the speed limit is exceeded just once thereby ensuring sufficient accuracy throughout catheter 10. For example, a workstation operator may retract guide wire 20 at a non-uniform speed. In this case, the speed criterion may be satisfied at certain times and may be violated at other times, while the same catheter 10 is being tracked.

Referring to FIGS. 1-2, from the description of the exemplary embodiments of the present invention, those having ordinary skill in the art will appreciate numerous benefits of an intervention system and method of the present invention including, but not limited to, (1) facilitating accurate treatment delivery by ensuring the quality of recorded tracking data during a shape reconstruction of an interventional tool (e.g., a catheter), particularly electro-magnetic tracking data, and (2) applicability to any interventional procedure that uses tracking, particularly electro-magnetic tracking, to map out shapes of interventional devices.

Furthermore, as one having ordinary skill in the art will appreciate in view of the teachings provided herein, features, elements, components, etc. described in the present disclosure/specification and/or depicted in the FIGS. 1 and 2 may be implemented in various combinations of electronic components/circuitry, hardware, executable software and executable firmware, particularly as application modules of a controller as described herein, and provide functions which may be combined in a single element or multiple elements. For example, the functions of the various features, elements, components, etc. shown/illustrated/depicted in the FIGS. 1 and 2 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for shape reconstruction of an interventional tool, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. An intervention system comprising:
an interventional tool having a lumen;
a sensor wire structurally configured to be manually translated within the lumen; and
a reconstruction controller,
wherein the reconstruction controller is structurally configured in communication with the sensor wire and configured to reconstruct a shape of the interventional tool responsive to a sensing of a manual translation of the sensor wire within the lumen, and
wherein the reconstruction controller is further configured to determine an accuracy of the reconstructed shape of the interventional tool based on translation velocities of the sensor wire within the lumen, wherein the translation velocities are determined by distances the interventional tool has moved between adjacent pairs of sensing points during the manual translation of the sensor wire within the lumen, wherein lesser spatial spacing between the adjacent pairs of sensing points is indicative of greater accuracy with which the shape of the interventional tool is reconstructed and larger spatial spacing between the adjacent pairs of sensing points is indicative of lower accuracy with which the shape of the interventional tool is reconstructed.

2. An intervention system comprising:
an interventional device having a lumen;
a guide wire configured to be manually translated within the lumen;
an electro-magnetic field generator configured to generate an electromagnetic field in the lumen;
a sensor mounted to the guide wire and adjacent a tip of the guide wire, the sensor being configured to sense the electro-magnetic field relative to a reference coordinate system with a fixed sensing frequency; and
one or more processors configured to:
receive sensed data from the sensor at a series of sensing points at the fixed sensing frequency,
determine translation velocities of the guide wire as the guide wire is manually translated within the lumen from the received sensed data between each of adjacent sensing points of the series of sensing points,
reconstruct a shape of the interventional device from the sensed data as the guide wire is manually translated within the lumen,
determine an accuracy of the reconstructed shape of the interventional device based on each of the translation velocities of the guide wire, wherein lower velocity is indicative of greater accuracy with which the shape of the interventional device is reconstructed and higher velocity is indicative of lower accuracy with which the shape of the interventional device is reconstructed by comparing each of the determined translation velocities with a first threshold, and
in response to the respective translation velocity being less than or equal to the first threshold, control a display device to generate a first indicator.

3. The intervention system of claim 2, wherein the interventional device is a catheter.

4. The intervention system of claim 2, wherein the one or more processors is configured to at least one of filter and smooth the received sensed data between at least three sensing points of manual translation of the guide wire within the lumen.

5. The intervention system of claim 2, wherein the one or more processors is further configured to:
compare the respective translation velocity with a second threshold, the second threshold being larger than the first threshold;
in response to the respective translation velocity meeting or exceeding the second threshold, control the display device to display a second indicator different from the first indicator, the second indicator indicating that the respective translation velocity of the guide wire is unacceptable as the guide wire is manually translated in the lumen.

6. The intervention system of claim 5, wherein the translation velocity of the guide wire within the lumen is indicative of a distance between the sensing points.

7. The intervention system of claim 5, wherein the one or more processors is further configured to:
in response to the respective translation velocity being between the first and second thresholds, control the display device to display a third indicator different from the first and second indicators.

8. The intervention system of claim 7, wherein:
the first indicator indicates that the respective translation velocity of the guide wire within the lumen is acceptable;
the second indicator indicates that the respective translation velocity of the guide wire in the lumen is unacceptable;
the third indicator indicates that the respective translation velocity of the guide wire in the lumen is borderline.

9. The intervention system of claim 7, wherein
the first indicator is color coded green,
the second indicator is color coded red, and
the third indicator is color coded yellow.

10. The intervention system of claim 7, wherein the one or more processors is further configured to:
control the display device to display the reconstructed shape of the interventional device; and
control the display device to color code portions of the displayed shape of the interventional device based on the first, second, and third indicators.

11. The intervention system of claim 5, wherein the one or more processors are further configured to:
control the display device to display the reconstructed shape of the interventional device and the first and second indicators in conjunction with one or more portions of the displayed reconstructed shape.

12. The intervention system of claim 2, wherein the one or more processors are further configured to
control the display device to display the reconstructed shape of the interventional device.

13. A reconstruction controller for an interventional procedure employing an interventional tool and a guide wire with an attached sensor manually translatable within a lumen of the interventional tool the sensor being configured to be sampled at fixed temporal intervals to output sensor signals at a plurality of sensing points indicative of a current location of the sensor relative to a reference frame, the reconstruction controller comprising:

one or more processors configured to:
reconstruct a shape of the interventional tool from the sensor signals output during manual translation of the guide wire with the attached sensor within the lumen, and
determine translation velocities of the sensor within the lumen between adjacent sensing points of the plurality of sensing points based on the sensor signals sampled at the fixed temporal intervals,
determine spatial spacing of the adjacent sensing points of the plurality of sensing points during the manual translation of the sensor within the lumen from the translation velocities of the sensor within the lumen and the fixed temporal intervals, wherein lesser spatial spacing between the sensing points is indicative of greater accuracy with which the shape of the interventional tool is reconstructed and larger spatial spacing between sensing points bcingis indicative of lower accuracy with which the shape of the interventional tool is reconstructed; and
generate indicators of accuracy with which portions of the shape of the interventional tool is reconstructed using the translation velocities.

14. The reconstruction controller of claim 13, wherein the one or more processors is further configured to control a display to display the indicators of the accuracy of the portions of the reconstructed shape of the interventional tool.

* * * * *